United States Patent [19]

Kemp, Jr.

[11] 4,004,000
[45] Jan. 18, 1977

[54] SELF-LIMITING CHEMICAL SYSTEMS FOR NONPOLLUTING CONTROL OF NOXIOUS PESTS

[75] Inventor: Robert T. Kemp, Jr., Asheville, N.C.

[73] Assignee: The United States of America as represented by the Secretary of the Navy, Washington, D.C.

[22] Filed: July 8, 1975

[21] Appl. No.: 594,409

[52] U.S. Cl. .............................. 424/200; 424/219; 424/223; 424/273; 424/333
[51] Int. Cl.$^2$ .......................................... A01N 9/36
[58] Field of Search .......... 424/219, 200, 333, 223; 210/310

[56] References Cited

UNITED STATES PATENTS

| 2,956,073 | 10/1960 | Whetstone et al. | 424/219 |
|---|---|---|---|
| 3,299,190 | 1/1967 | Schrader | 424/219 |

OTHER PUBLICATIONS

Chemical Abstracts, vol. 73 (1970), p. 66574d.
Chemical Abstracts, vol. 78 (1973), p. 43354w.

Primary Examiner—V. D. Turner

[57] ABSTRACT

A method for producing a non-polluting toxic principle for use as a pesticide comprising combining at least two relatively stable reactants to form a non-stable toxic principle, said reactants being combined just prior to actual use of the principle.

10 Claims, 2 Drawing Figures

FIG. 1 (TABLE I)

BINARY CHEMICAL SPRAY SYSTEM TESTS

| TEST COMPOUNDS | CONCENTRATION (1) (ppm) (9) | TEST SPECIES | KILL RATIO AT ELAPSED TIME (MIN.) 3 | 15 | 300 |
|---|---|---|---|---|---|
| DDVP (2) | 500 | AM. ROACH | 0/5 | 3/5 | 3/5 |
| PYRETHRINS (3) | 6000 | AM. ROACH | 0/5 | 5/5 | |
| TMP + CHLORAL (4) | 500 | AM. ROACH | 3/5 | 5/5 | |
| TMP + CHLORAL (4) | 50 | AM. ROACH | 3/5 | 5/5 | |
| TMP + CHLORAL (4) | 50 | MOUSE (5) | 0/5 | 0/5 | 0/5 |
| TMP + 2K39 (6) | 15 | HOUSE FLY | 1/10 | 2/10 | 10/10 |
| CHLORAL | 500 | AM. ROACH | 0/5 | 0/5 (7) | 3/5 |
| TMP (8) | 500 | AM. ROACH | 0/5 | 4/5 | 4/5 |
| KEROSENE | | AM. ROACH | 0/5 | 0/5 | 0/5 |

(1) KEROSENE SOLVENT, FREON ($CC1_2F_2$) PROPELLANT.

(2) TECHNICAL VAPONA, DIMETHYL DICHLOROVINYL PHOSPHATE.

(3) USDA 1783-40, INSECTICIDE, AEROSOL SYNERGIZED PYRETHRUM.

(4) BINARY DDVP (5) NO EVIDENCE OF TOXICITY TO MICE. THE TEST ANIMALS THOROUGHLY LICKED THEIR COATS WHICH HAD BEEN DRENCHED WITH BINARY SPRAY.

(6) BINARY DIMETHYL 2,2 - DICHLORO - 1 -(3,5 - DIPHENYLPYRAZOLYL)VINYL PHOSPHATE.

(7) QUIET, APPEAR TO BE DRUGGED, BUT NOT DEAD.

(8) TRIMETHYL PHOSPHITE.

(9) PARTS PER MILLION

NOTE: (4) and (6) are formulas for the toxic principles produced by the reactions between TMP + CHLORAL; TMP + 2K39; respectively.

FIG. II (TABLE II) (1,2)

| TEST COMPOUND(S) | CONCEN-TRATION (ppm) | AMERICAN ROACH 15 MIN. | AMERICAN ROACH 24 HR. | HOUSE FLY 15 MIN. | HOUSE FLY 24 HR. | MEX. BEAN BEETLE 15 MIN. | MEX. BEAN BEETLE 24 HR. | GRAPE PELIDONTA 15 MIN. | GRAPE PELIDONTA 24 HR. |
|---|---|---|---|---|---|---|---|---|---|
| | | KILL RATIO | KILL RATIO | KILL RATIO | KILL RATIO | KILL RATIO | KILL RATIO | KILL RATIO | KILL RATIO |
| TMP + CHLORAL (3) | 76 | 3/11 | 11/11 | 0/159 | 0/159 | | | | |
| TMP + 2K52 (4) | 99 | 5/11 | 11/11 | 0/131 | 0/131 | | | | |
| TMP + 2K39 (5) | 76 | 3/10 | 10/10 | 0/133 | 0/133 | 11/11 | 11/11 | 4/4 | 4/4 |
| TMP + 2K39 (5) | 76 | 5/10 | 10/10 | 75/101 (6) | 91/101 | 11/11 | 11/11 | | |
| CONTROL (NO TREATMENT) | 0 | 0/10 | 0/10 | 0/130 | 0/130 | | | | |

(1) ALL INSECTS WERE IN THE ADULT STAGE EXCEPT THE COCK ROACHES, WHICH WERE NYMPHS AND ADULTS.

(2) ALL INSECTS WERE SPRAYED DIRECTLY EXCEPT THE HOUSE FLIES IN THE FIRST THREE TESTS.

(3) BINARY DDVP.

(4) BINARY DIMETHYL 2,2 - DICHLORO - 1 - PYRAZOLYLVINYL PHOSPHATE (THE TOXIC PRINCIPLE PRODUCED BY THE REACTION BETWEEN TMP AND 2K52)

(5) BINARY DIMETHYL 2,2 - DICHLORO - 1 - (3,5 - DIPHENYLPYRAZOLYL)VINYL PHOSPHATE (THE TOXIC PRINCIPLE PRODUCED BY THE REACTION BETWEEN TMP AND 2K39)

(6) AFTER 60 MINUTES

BINARY CHEMICAL SPRAY SYSTEM TESTS
FOR EFFECTIVENESS AGAINST INSECTS (1,2)

SELF-LIMITING CHEMICAL SYSTEMS FOR NONPOLLUTING CONTROL OF NOXIOUS PESTS

BACKGROUND OF THE INVENTION

This invention relates to chemical control of pests and especially to a system for non-polluting control of pests.

Many of the pesticides upon which we depend heavily, such as DDT, used for the control of malaria-bearing mosquitos and for the protection of our crops, are now banned because of persistence in the environment and ecological damage. The less persistent organophosphorus and carbamate chemicals have been substituted for the banned materials, but some are more acutely toxic than DDT and have resulted in fatal accidents. Consequently, there are requirements for safer and less persistent means of pest control. Several alternatives to toxic chemicals have been proposed and used effectively. These are: (1) biological control (the use of predator species); (2) sterilization (dissemination of sterile males to cause infertile matings); (3) sex lures and baits (to attract pests into traps); and (4) pest-resistant strains (development of strains of crops and domestic animals which have a physiological resistance to the pests). Although these methods are very effective in specific applications, there are many pests for which such specific means of control have not been provided or for which these means are not economically feasible. A safe chemical method compatible with the environment, economically feasible and of general applicability is desirable.

With chemicals, there is a limit to the degree of non-persistence that can be achieved, because a substantial shelf-life is required for the practical distribution and use of chemical pesticides. A pesticidal system in which the product is synthesized at the site of application, however, has no shelf-life constraint and if non-toxic reactants are employed in such systems, they are capable of being both safe and non-polluting.

SUMMARY OF THE INVENTION

The objects and advantages of the present invention are accomplished by combining relatively non-toxic, stable ingredients at the place of application to form a toxic, non-stable principle.

An object of this invention is to control pests chemically without polluting the environment.

Another object is to produce a toxic, non-stable, chemical pesticide which is employable at its most effective stage chemically.

Other objects, advantages and novel features of the present invention will become apparent from the following detailed description of the invention when considered in conjunction with the accompanying drawing.

BRIEF DESCRIPTION OF THE FIGURE

FIG. 1 is a table showing the results of binary chemical spray system tests with certain binary chemicals compared to individual insecticides.

FIG. 2 is a table showing the kill ratio results of binary spraying with some chemicals.

DETAILED DESCRIPTION OF THE INVENTION

The method of the present invention is to combine relatively non-toxic, stable, reactant ingredients, or reactants, at the insect infested target area at which they are to be employed to kill pests. The reactants must be such as will chemically react to produce an insecticidal, non-stable (i.e., non-persistent) principle.

Tables I and II show three binary (two active ingredients) systems which can be used. The first employs as active reactants Trimethyl Phosphite and chloral. The second employs TMP and 2K39 (3, 5-diphenyl-N-(trichloroacetyl) pyrazole) and the third employs TMP and 2K52 (N (trichloroacetyl) pyrazole). These are binary systems employing two active reactants; other systems may employ more than two.

The systems are compared in the tables with each other and with other types of pesticides. Thus, in Table I, DDVP is indicated to have killed 0 out of 5 roaches after 3 minutes but 3 out of 5 after 15 minutes. TMP plus chloral kills 3 out of 5 roaches at the end of 3 minutes and all at the end of 15 minutes.

In Table II, it can be seen, for example, that TMP and chloral will kill 3 roaches for every 11 at the end of 15 minutes.

If TMP and chloral are combined in the ratio of 208 to 147 grams, 305 grams of the insecticidal principle will be formed; 208 grams of TMP to 366 grams of 2K39 gives 524 grams of insecticidal principle known as Binary Dimethyl 2,2-Dichloro-1-(3,5-Diphenyl-pyrazolyl) Vinyl Phosphate; 208 grams of TMP to 213 grams of 2K52 gives 371 grams of insecticidal principle known as Binary Dimethyl 2,2 Dichloro-1-Pyrazolylvinyl Phosphate. The formulas for the insecticidal principles and other test data are given in Tables I and II below.

Various methods of combining the active reactants to form the toxic insecticidal principle may be employed. For example, a spray device may be used which has two spray nozzles and is constructed so that the two streams from the nozzles intersect. Or two separate spray devices may be used in time series (i.e. one after another) to spray the same area. Or the active reactants can be placed in the same container and mixed just prior to the spraying.

The greater effectiveness of the binary spray system over the conventional pesticide may be attributable to the highly reactive character of the nascent product, i.e., it is to be expected that the insecticidal principle will have more high-energy molecules just after its formation. The binary systems are safer because non-toxic ingredients are used to form toxic products which are intrinsically unstable and therefore self-limiting with respect to toxicity.

The binary reaction can be limited to liquid-phase reactions employing spray droplets too heavy to drift, thus preventing contamination of areas adjacent to the target. Note data in Table II which shows that flies in the area, but not under direct spray, were not killed.

A further advantage of the self-limiting character of the binary product is that it provides the means to achieve the ultimate degree of non-persistence and ecological compatibility that can be obtained with chemicals.

Obviously, many modifications and variations of the present invention are possible in light of the above teachings. It is therefore to be understood that, within the scope of the appended claims, the invention may be practiced otherwise than as specifically described.

What is claimed is:

1. A method of controlling insects comprising applying to the locus of said insects an insecticidally effective amount of a non-polluting insecticidal principle formed by spraying a first relatively non-toxic, stable reactant, trimethyl phosphite, from one nozzle; and spraying a second non-toxic, stable reactant selected from the group consisting of chloral, 3,5-diphenyl-N-(trichloroacetyl) pyrazole, and N(trichloroacetyl) pyrazole from a second nozzle, so as to cause said first and said second reactants to combine to form a non-stable insecticidal principal.

2. The method of claim 1, wherein the step of combining the reactants comprises spraying said reactants in individual intersecting streams.

3. The method of claim 2, wherein said sprays are in the form of heavy droplets so that they remain in the sprayed area.

4. The method of claim 1, wherein the step of combining the reactants comprises individually spraying each of the reactants over an insect infested target area in time series.

5. A method as in claim 1, wherein the reactants are trimethyl phosphite and chloral.

6. A method as in claim 1, wherein the reactants are trimethyl phosphite and 3,5-diphenyl-N-(trichloroacetyl) pyrazole.

7. A method as in claim 1, wherein the reactants are trimethyl phosphite and N (trichloroacetyl) pyrazole.

8. The method of claim 5, wherein said reactants are combined in a ratio of 208 grams of trimethyl phosphite to 147 grams of chloral to form Binary Dimethyl Dichlorovinyl Phosphate as said toxic principle.

9. The method of claim 6, wherein said reactants are combined in a ratio of 208 grams of trimethyl phosphite to 366 grams of 3,5 diphinyl-N- (trichloroacetyl) pyrazole to form Binary Dimethyl 2,2-Dichloro-1-(3,5 Diphenylpyrazolyl) Vinyl Phosphate as said toxic principle.

10. The method of claim 7, wherein said reactants are combined in a ratio of 208 grams of trimethyl phosphite to 213 grams of N (trichloroacetyl) pyrazole to form Binary Dimethyl 2,2-Dichloro-1-Pyrazolylvinyl Phosphate as said toxic principle.

* * * * *